(12) United States Patent
Chiffey et al.

(10) Patent No.: US 7,832,203 B2
(45) Date of Patent: Nov. 16, 2010

(54) EXHAUST SYSTEM FOR A LEAN BURN INTERNAL COMBUSTION ENGINE

(75) Inventors: Andrew Francis Chiffey, Ware (GB); Paul Richard Phillips, Royston (GB)

(73) Assignee: Johnson Matthey Public Limited Company, London (GB)

( * ) Notice: Subject to any disclaimer, the term of this patent is extended or adjusted under 35 U.S.C. 154(b) by 123 days.

(21) Appl. No.: 11/281,089

(22) Filed: Nov. 17, 2005

(65) Prior Publication Data

US 2006/0133969 A1 Jun. 22, 2006

Related U.S. Application Data

(63) Continuation-in-part of application No. 10/494,406, filed as application No. PCT/GB02/04750 on Oct. 21, 2002, now abandoned.

(30) Foreign Application Priority Data

Oct. 27, 2001 (GB) .................................. 0125890.4

(51) Int. Cl.
*F01N 3/00* (2006.01)
(52) U.S. Cl. .............................. 60/297; 60/274; 60/295; 60/301; 60/311
(58) Field of Classification Search .................. 60/274, 60/295, 297, 311, 301; 422/168, 177; 423/212, 423/213.2, 213.5, 239.1, 247
See application file for complete search history.

(56) References Cited

U.S. PATENT DOCUMENTS

| | | | | |
|---|---|---|---|---|
| 4,902,487 | A | * | 2/1990 | Cooper et al. ............ 423/215.5 |
| 5,206,202 | A | * | 4/1993 | Lachman et al. ............ 502/216 |
| 5,213,781 | A | * | 5/1993 | Abe et al. ................. 423/239.1 |
| 5,746,989 | A | * | 5/1998 | Murachi et al. .......... 423/213.7 |
| 6,413,483 | B1 | | 7/2002 | Brisley et al. |
| 6,753,294 | B1 | * | 6/2004 | Brisley et al. ................ 502/439 |
| 6,855,297 | B2 | * | 2/2005 | Van Den Bussche et al. ..... 422/177 |
| 6,863,874 | B1 | * | 3/2005 | Twigg ........................ 423/210 |

FOREIGN PATENT DOCUMENTS

| | | |
|---|---|---|
| DE | 196 36 041 A1 | 3/1998 |
| DE | 199 41 439 A1 | 3/2000 |
| EP | 0 341 832 B1 | 11/1989 |
| EP | 0 560 991 A1 | 9/1993 |

(Continued)

*Primary Examiner*—Thomas E Denion
*Assistant Examiner*—Diem Tran
(74) *Attorney, Agent, or Firm*—RatnerPrestia

(57) ABSTRACT

An exhaust system for an internal combustion engine has a catalyzed ceramic wall flow particulate filter coated with a washcoat composition. The washcoat composition includes an oxidation catalyst of at least one platinum group metal and a $NO_x$ absorbent. The washcoat composition has a D50 of less than or equal to 8 μm. The $NO_x$ absorbent absorbs $NO_x$ contained in an exhaust gas when the composition of the exhaust gas is lambda >1, and releases the $NO_x$ absorbed in the $NO_x$ absorbent when the exhaust gas composition is 1≧lambda. The exhaust system has a platinum group metal catalyst upstream of the filter for oxidizing NO to $NO_2$ at least when the composition of the exhaust gas is lambda >1. The uncoated portions of the ceramic wall flow particulate filter have a porosity of >40% and a mean pore size of 8-25 μm.

20 Claims, 1 Drawing Sheet

FOREIGN PATENT DOCUMENTS

| | | |
|---|---|---|
| EP | 0 758 713 A1 | 2/1997 |
| EP | 0 893 154 A2 | 1/1999 |
| EP | 0 984 146 A2 | 3/2000 |
| EP | 1 008 379 A1 | 6/2000 |
| EP | 1 033 161 A1 | 9/2000 |
| EP | 1 079 084 A2 | 2/2001 |
| EP | 1 108 460 A1 | 6/2001 |
| JP | 9-53442 A | 2/1997 |
| JP | 2722987 B2 | 3/1998 |
| JP | 2001-173426 A | 6/2001 |
| JP | 2001-207836 A | 8/2001 |
| JP | 2001-227324 A | 8/2001 |
| WO | WO-00/21647 | 4/2000 |
| WO | WO 01/12320 * | 2/2001 |
| WO | WO-02/18753 A1 | 3/2002 |

\* cited by examiner

EXHAUST SYSTEM FOR A LEAN BURN INTERNAL COMBUSTION ENGINE

CROSS REFERENCE TO RELATED APPLICATIONS

This application is a continuation-in-part application of U.S. patent application Ser. No. 10/494,406, filed May 3, 2004, which is the U.S. National Phase application of PCT International Application No. PCT/GB02/04750, filed Oct. 21, 2002, and claims priority of British Patent Application No. 0126346.6, filed Nov. 2, 2001.

BACKGROUND OF THE INVENTION

The present invention relates to an exhaust system for a lean burn internal combustion engine, and in one illustrative embodiment, to an exhaust system for a diesel engine.

Lean burn internal combustion engines, such as diesel engines and gasoline engines, produce a number of pollutants including carbon monoxide (CO), unburnt hydrocarbon (HC), particulate matter (PM) and nitrogen oxides ($NO_x$). Whilst not as visible to the naked eye as PM emitted by diesel engines, gasoline engines produce PM of the size-order of <1 μm such as 10-100 nm. Interest in gasoline PM is growing as particles of this size can penetrate deep into the human lungs and can be detrimental to health.

The amount of these pollutants that can be emitted by vehicular internal combustion engines is prescribed by legislation in various countries and regions of the world, such as the USA and Europe, and these amounts are set to decrease as the legislation tightens step-wise over the next ten years or so. Similarly, International agreements between countries have led to moves toward vehicular internal combustion engines that use fuel more efficiently. The legislation acts as a stimulus to vehicle manufacturers and to their suppliers to devise new engines that are more fuel-efficient and that emit fewer pollutants and to exhaust systems that can clean up the exhaust gas before it passes to atmosphere.

One such exhaust system component primarily for treating diesel exhaust comprises an oxidation catalyst for oxidising NO in the exhaust gas to $NO_2$ and a downstream filter for trapping PM. A process for treating diesel PM that uses this arrangement is described in EP-B-0341382 or U.S. Pat. No. 4,902,487, both of which are incorporated herein by reference. The process claimed in EP-B-0341382 comprises passing an exhaust gas, such as a diesel exhaust gas, including PM and NO unfiltered over an oxidation catalyst to convert the NO to $NO_2$, collecting soot on the filter and combusting the collected soot by reaction with the $NO_2$. This technology is commercially available as Johnson Matthey's Continuously Regenerating Trap or CRT®. Further steps may be added, for example downstream $NO_x$ removal by injection of reductant e.g. HC or $NO_x$-specific reactant e.g. $NH_3$ or urea (see for example our WO-A-00/21647, incorporated herein by reference). An advantage of this process is that it is possible to combust diesel soot at temperatures of up to 400° C., whereas combustion of diesel soot in oxygen occurs at about 500° C. This is significant since diesel exhaust gas is generally cooler than exhaust gas from gasoline engines and soot would accumulate on the filter causing back-pressure problems in the system if the process relied on combustion of soot in oxygen.

One form of gasoline engine is a gasoline direct injection engine, which is designed to operate under stoichiometric and lean conditions. When running lean, relatively low levels of $NO_x$ are formed that cannot be reduced (removed) in the presence of the relatively high levels of oxygen in the exhaust gas. Reducing species, e.g. HC, can reduce $NO_x$ to $N_2$ during stoichiometric- or rich-running conditions, as comparatively less oxygen is present than during lean-running conditions.

In order to control $NO_x$ in lean-burn engines, there has been devised a $NO_x$ absorber/catalyst which can store $NO_x$, e.g. as nitrate, when an engine is running lean. In a stoichiometric or rich environment, the nitrate is understood to be thermodynamically unstable, and the stored $NO_x$ is released and is reduced by the reducing species present in the exhaust gas. This $NO_x$ absorber/catalyst is commonly called a $NO_x$-trap and is described in EP-A-0560991 (the entire contents of which is incorporated herein by reference). By periodically controlling the engine to run stoichiometrically or rich, stored $NO_x$ is reduced and the $NO_x$-trap regenerated.

A typical $NO_x$-trap formulation comprises a washcoat comprising a catalytic oxidation component, such as platinum, a $NO_x$-storage component, such as barium, and a reduction catalyst e.g. rhodium on a surface area-enhancing support material, e.g. a metal oxide such as alumina, or a mixed or composite (i.e. not a mixed phase pure) metal oxide containing one or more of aluminium, zirconium, titanium, cerium, silicon and chromium. One mechanism commonly given for $NO_x$-storage during lean engine operation for this formulation is:

$$NO + \tfrac{1}{2}O_2 \rightarrow NO_2; \text{ and} \quad \text{(i)}$$

$$BaO + NO_2 + \tfrac{1}{2}O_2 \rightarrow Ba(NO_3)_2. \quad \text{(ii)}$$

In the first step, the nitric oxide reacts with oxygen on active oxidation sites on the platinum to form $NO_2$. The second step involves adsorption of the $NO_2$ by the storage material in the form of an inorganic nitrate.

When the engine runs under rich conditions or at elevated temperatures, the nitrate species become thermodynamically unstable and decompose, producing NO or $NO_2$ according to equation (iii) below. Under rich conditions, these nitrogen oxides are subsequently reduced by carbon monoxide, hydrogen and hydrocarbons to $N_2$, which can take place over the reduction catalyst.

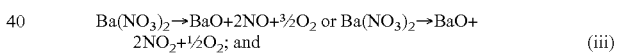

$$Ba(NO_3)_2 \rightarrow BaO + 2NO + \tfrac{3}{2}O_2 \text{ or } Ba(NO_3)_2 \rightarrow BaO + 2NO_2 + \tfrac{1}{2}O_2; \text{ and} \quad \text{(iii)}$$

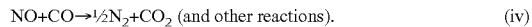

$$NO + CO \rightarrow \tfrac{1}{2}N_2 + CO_2 \text{ (and other reactions).} \quad \text{(iv)}$$

In the reactions of (i)-(iv) above the reactive barium species is given as the oxide. However, it is understood that in the presence of air most of the barium is in the form of the carbonate or possibly the hydroxide. The above reaction schemes can be adapted accordingly for species of barium other than the oxide.

$NO_x$-traps are typically coated on a flow through honeycomb monolith substrates. One form of such substrate is made from a ceramic material such as cordierite. Typical commercially available flow-through monolith substrates have a mean pore size of 3 μm and a porosity of about 35%. $NO_x$-trap washcoat formulations for coating on flow through honeycomb monolith substrates have a D50, of about 15 μm, i.e. at least 50% of the particle sizes in the washcoat are 15 μm in diameter or less. Similarly a D70, would mean that at least 70% of the particle sizes in the washcoat are 15 μm in diameter or less.

Using sophisticated engine management techniques to provide for rich/lean cycling and common rail fuel injection, vehicle manufacturers are now adopting $NO_x$-trap technology into diesel exhaust systems. One such system is described in EP-A-0758713 (the entire contents of which is incorporated herein by reference). Means for reducing the redox composition of the exhaust gas, as defined by lambda, for the purpose of regenerating a $NO_x$-trap include injecting HC into the exhaust gas downstream of the engine, adjusting the ignition timing of at least one engine cylinder or adjusting the engine air-to-fuel ratio. Since the $NO_x$ trap disclosed in EP-A-0758713 comprises a flow through monolith substrate, it can be assumed that the substrate porosity and mean pore size of the substrate and the D50 of the washcoat composition will be in the order of that mentioned above.

Where a $NO_x$-trap formulation comprises a reduction catalyst such as rhodium, it is known to locate the $NO_x$-trap components where they can maximise their activity, i.e. of the oxidation catalyst component, e.g. platinum, to oxidise NO to $NO_2$ and HC and CO during lambda >1 conditions; and for the rhodium to catalyse the reduction of $NO_x$ to $N_2$ with HC during $1 \geq$ lambda conditions. One such arrangement is disclosed in U.S. Pat. No. 6,413,483 (the entire contents of which is incorporated herein by reference), wherein the rhodium component is in an overlayer on a layer containing the Pt component.

Another technique that can be used to control emissions is exhaust gas recirculation (EGR). In this, a portion of the exhaust gas is taken returned to the engine air intake so that the engine is fed a mixture of air and exhaust gas. Because the resulting mixture is lower in oxygen than in air, the temperature of the combustion event is reduced so that there is less $NO_x$ in the exhaust gas. This technique does cause an increase in PM, so there is a pay-off between $NO_x$ and PM, but by managing the rate of EGR to the load on the engine, it is possible to obtain an overall reduction in pollutant emissions.

In Japanese Patent No. 2722987 and EP-A-1079084 (the entire contents of which documents are incorporated herein by reference), Toyota describes an exhaust system including a component including a combination of certain of the catalyst features described above. Essentially it describes a catalysed particulate trap including a $NO_x$-trap. In particular, the component comprises a particulate trapping device comprising a $NO_x$ absorbent capable of absorbing $NO_x$ contained in exhaust gas when the air-fuel ratio of the exhaust gas is lean, and capable of releasing the $NO_x$ absorbed in the $NO_x$ component when the air-fuel ratio of the exhaust gas is substantially equal to the stoichiometric air-fuel ratio or rich. One method of coating a particulate filter with a catalyst washcoat is disclosed in EP-A-0766993 (the entire contents of which is incorporated herein by reference). The method of this patent provides a coating layer which is uniformly formed on the surfaces of the pores in the porous walls of the wall-flow filter and the catalyst is carried thereon.

In JP-B-2722987, the mechanism suggested for the combustion of soot trapped on the particulate trap is that during lean running, a high concentration of oxygen $O_2$ is deposited in the form of $O_2^-$ or $O^{2-}$ on the surface of platinum (Pt). NO contained in the flowing exhaust gas reacts with $O_2^-$ or $O^{2-}$ on the surface of the Pt to form $NO_2$ ($2NO+O_2 \rightarrow 2NO_2$). Then, part of the $NO_2$ thus formed is absorbed into the $NO_x$ absorbent while being oxidised on Pt, and diffused in the form of nitrate ion $NO_3^-$ while combining with BaO.

If the air-fuel ratio is adjusted rich, the oxygen concentration in the exhaust gas is reduced, and consequently the amount of $NO_2$ formed on the surface of the Pt is reduced. If the amount of $NO_2$ produced is reduced, the reaction proceeds in the reverse direction ($NO_3^- \rightarrow NO_2$) and thus the nitrate ion $NO_3^-$ is released in the form of $NO_2$ from the absorbent.

The suggestion is that "activated oxygen" species such as $O_2^-$ and $O^{2-}$ are responsible for combusting particulate during rich and lean running, but also that $NO_2$ could also be responsible for combustion of particulate, particularly during rich running.

We have investigated Toyota's combined particulate filter-$NO_x$ trap and have found, very surprisingly, that by introducing an oxidation catalyst active for oxidation of NO to $NO_2$ upstream of the filter/trap in a similar arrangement to that described in EP-B-0341382 or U.S. Pat. No. 4,902,487 that filter regeneration is improved compared with filter regeneration employing the particulate filter-$NO_x$ trap alone. We have been able to show this by measuring the back-pressure in the system on a bench mounted engine. Increased back-pressure is an indication of increased particulate build up, i.e. that particulate deposition and particulate combustion are not in balance. It is also believed that the system represents an improvement over the system described in EP-A-758713 in that $NO_x$ released from the $NO_x$ absorbent can combust trapped particulate, but also oxidise HC to carbon dioxide ($CO_2$) and water ($H_2O$) and oxidise carbon monoxide CO to $CO_2$. Accordingly, the system provides an improved management of pollutant species in the exhaust gas.

SUMMARY OF THE INVENTION

According to the invention, there is provided an exhaust system for an internal combustion engine, which system comprising a catalysed ceramic wall flow particulate filter coated with a washcoat composition comprising an oxidation catalyst comprising at least one platinum group metal selected from the group consisting of platinum and palladium and a $NO_x$ absorbent comprising at least one metal selected from the group consisting of alkali metals, alkaline earth metals and rare earth metals for absorbing $NO_x$ contained in an exhaust gas when the composition of the exhaust gas is lambda >1, and for releasing the $NO_x$ absorbed in the $NO_x$ absorbent when the exhaust gas composition is $1 \geq$ lambda, and a platinum group metal catalyst upstream of the filter for oxidising NO to $NO_2$ at least when the composition of the exhaust gas is lambda >1, wherein the uncoated ceramic wall flow particulate filter has a porosity of >40% and a mean pore size of 8-25 µm and the D50 of the washcoat composition is less than or equal to 8 µm.

DETAILED DESCRIPTION OF THE INVENTION

Figure 1:
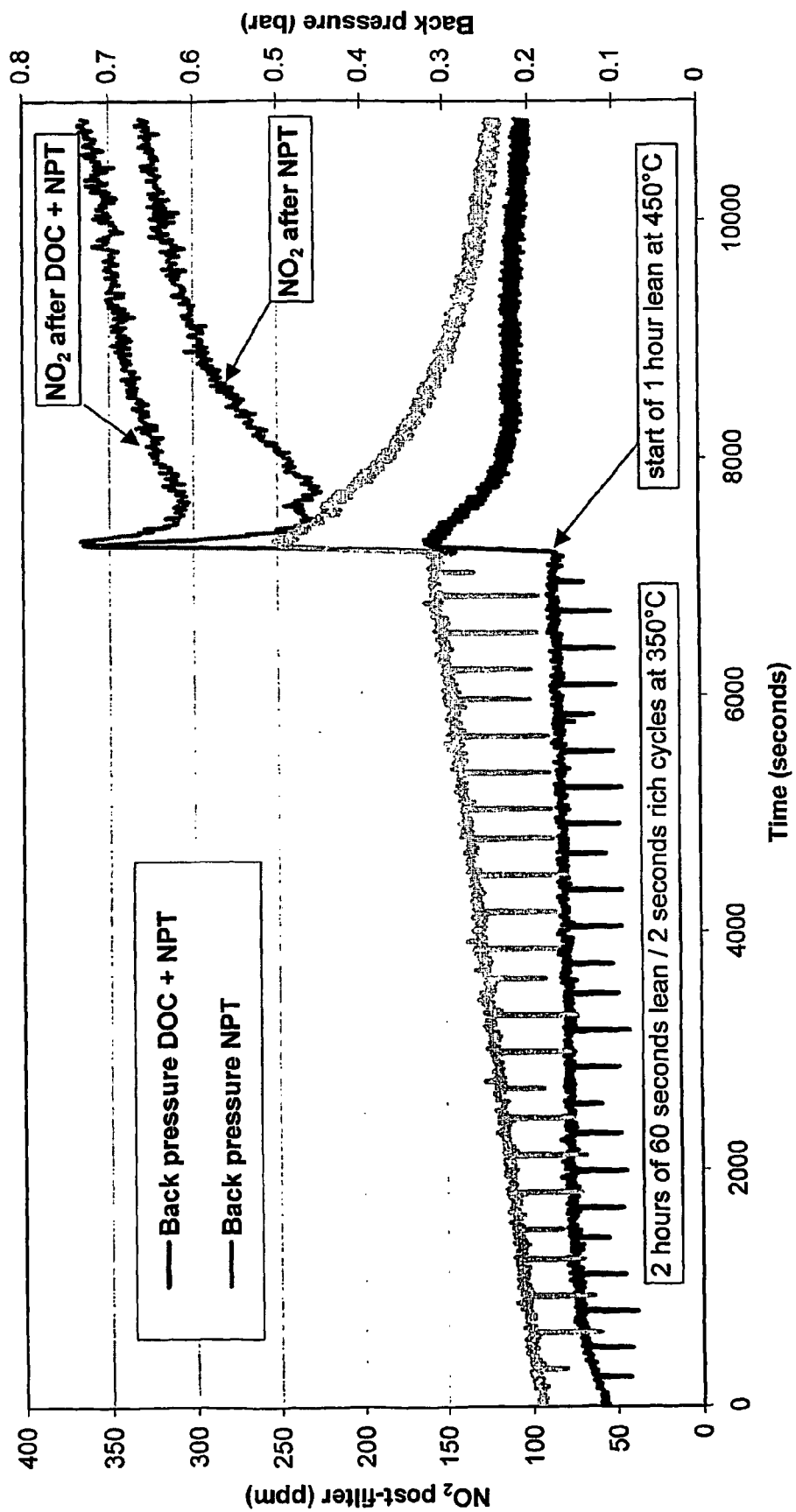
FIG. 1 is a plot of the amount of post-filter $NO_x$ (ppm) over time.

One theory that an exhaust system including the particulate filter-$NO_x$ trap alone is less active for particulate combustion is because the combustion of trapped particulate occurs only where it is in contact with the Pt or other washcoat components. Accordingly, particulate further from the surface of the filter-trap is combusted later than that which is nearer the surface. In the present invention particulate in contact with the Pt on the trap can be combusted at the same time as particulate not in contact with the Pt, because the particulate not in contact with the Pt is combusted in exhaust gas including increased levels of $NO_2$ downstream of the oxidation catalyst.

The invention is advantageous in that by reducing back-pressure in the system, fuel economy is improved and wear on the engine is reduced or eliminated.

In one embodiment the porosity of the uncoated filter is from 42-60%.

In another embodiment, the mean pore size of the uncoated filter is from 11-22 µm.

Known catalysts for producing $NO_2$ from NO and $O_2$ may be used to generate the $NO_2$ oxidant for the purpose of combusting particulate. Such catalysts are extensively used in the catalytic conversion of automotive exhaust gases. This includes, for example, Pt, rhodium (Rh), ruthenium (Ru), palladium (Pd) or combinations thereof, platinum group metal oxides such as $RhO_3$ and the like. Conveniently, the catalyst is coated onto a monolith substrate e.g. a ceramic or metal honeycomb.

The filter may be in conventional form and structure. Typically this comprises a ceramic wall-flow filter of appropriate pore size, but one or more wire meshes of appropriate metal e.g. stainless steel or the like can also be used.

The $NO_x$ absorbent includes alumina, for example as a support, and at least one selected from, for example, alkali metals, such as potassium (K), sodium (Na), lithium (Li) and caesium (Cs), alkaline earth metals, such as barium (Ba) and calcium (Ca), and rare earth metals, such as lanthanum (La) and yttrium (Y), and a noble metal such as Pt carried on the support. A reduction catalyst such as rhodium can also be included. In a particular embodiment, the rhodium is coated on the exit channels of the filter.

According to a further aspect, the invention provides an internal combustion engine including an exhaust system according to the invention. The engine can be a diesel engine, such as a heavy duty diesel engine (as defined by the relevant European or US Federal or California State legislation) or a diesel engine for a light duty diesel engine, such as for a passenger vehicle or van. The engine can also be a gasoline engine, such as a lean-burn gasoline engine including a gasoline direct injection engine. However, the engine can be powered by alternative fuel means such as CNG, LPG or methanol, and engines powered by these alternative fuels are within the scope of the present invention.

In a further aspect, the invention comprises a vehicle including an internal combustion engine according to the invention. However, the exhaust system can be also be used in connection with stationary power plants.

According to a further aspect, the invention provides a method of treating an exhaust gas of an internal combustion engine, which method comprising oxidising NO in the exhaust gas to $NO_2$ at least when the composition of the exhaust gas is lambda >1, trapping particulate on a catalysed ceramic wall flow filter coated with a washcoat including a $NO_x$ absorbent, oxidising NO to $NO_2$ on the filter when the composition of the exhaust gas is lambda >1, absorbing the $NO_2$ in the $NO_x$ absorbent when the composition of the exhaust gas is lambda >1, releasing the absorbed $NO_x$ as $NO_2$ when the exhaust gas composition is $1 \geq lambda$ and combusting particulate trapped on the filter in $NO_2$ wherein the step of oxidising NO to $NO_2$ is performed upstream of the filter and wherein the uncoated ceramic wall flow particulate filter has a porosity of >40% and a mean pore size of 8-25 µm and wherein the D50 of the washcoat composition is less than or equal to 8 µm.

In order that the invention may be more fully understood, the following Example is provided by way of illustration only and with reference to the accompanying Figure which shows a graph depicting the effect of pre-NO oxidation catalyst and combined $NO_x$ and particulate trap.

EXAMPLE

A diesel particulate wall-flow filter (5.66 inches (14.38 cm) diameter by 6 inches (15.24 cm) long, 200 cells per square inch (31 cells $cm^{-2}$)) was coated with a conventional $NO_x$ trap composition comprising supported platinum and barium prepared using known incipient wetness solution impregnation and conventional coating techniques. The coated filter was dried in an airflow and calcined at 500° C.

The resulting piece, now termed a $NO_x$ particulate trap (NPT), was mounted in a stainless steel can using standard procedures, and fitted to the exhaust gas system of a bench-mounted 1.9 liter common rail diesel engine. The engine was coupled to a dynamometer in the conventional manner, with both engine and dynamometer being controlled by computer. Exhaust emissions at pre- and post-NPT positions were measured at 10 second intervals. Gas pressures and temperatures at pre- and post-NPT positions were measured over the same time interval.

The engine was operated to give cycles of lean-running and rich-running conditions. The engine was run at 2300 rpm and the torque was adjusted to give a NPT gas inlet temperature of 350° C. After 60 seconds of lean-running the engine conditions were changed to rich conditions for 2 seconds by means of fuel post-injection, air intake throttling, and increased exhaust gas recirculation (EGR) rate. After two hours of cycling 60 seconds lean and 2 seconds rich the engine was kept at lean-running conditions and the torque was increased to give a NPT gas inlet temperature of 450° C. These lean-running conditions were maintained for 1 hour. The reaction between soot and $NO_2$ during this period was monitored by the reduction in back pressure of the system.

The above test conditions were repeated on a combined system comprising of diesel oxidation catalyst (DOC) followed by a NPT filter.

The DOC was prepared by coating a cordierite monolith (5.66 inches (14.38 cm) diameter by 3 inches (7.62 cm) long, 400 cells per square inch (62 cells $cm^{-2}$)) with platinum supported on alumina using conventional coating techniques. The DOC was mounted in a stainless steel can and fitted to the exhaust gas system of the diesel engine. The NPT filter was then fitted 1 inch (2.54 cm) behind the DOC. Emissions and back pressure measurements were carried out over the lean-rich cycling and lean only conditions detailed above.

As can be seen from FIG. 1, during the rich-lean cycling, the back-pressure in the system including the DOC upstream of the NPT is consistently lower than the back-pressure in the system without the DOC. Furthermore, it can be seen that following the switch to constant lean running, $NO_2$ increases downstream of the NPT in both systems. This is because the $NO_x$ absorbent is "full" or substantially all the $NO_x$ absorbent is in the nitrate form. With no rich regeneration events to reduce the nitrate and regenerate the $NO_x$ absorbent, the system including the DOC+NPT essentially becomes a CRT as described in EP-B-341832. $NO_2$ generated over the Pt of the $NO_x$ trap on the NPT appears to be responsible for the combustion of particulate on the NPT only system. In both cases, increased $NO_2$ is detected downstream of the NPT.

What is claimed is:

1. An exhaust system for an internal combustion engine, which system comprising:
   a catalysed ceramic wall flow particulate filter coated throughout with a washcoat composition, the washcoat composition comprising
   an oxidation catalyst comprising a platinum group metal selected from the group consisting of platinum, palladium, and a mixture thereof, and
   a $NO_x$ absorbent comprising a metal selected from the group consisting of an alkali metal, an alkaline earth metal, a rare earth metal, and a mixture thereof for absorbing $NO_x$ contained in an exhaust gas when the composition of the exhaust gas is lambda>1, and for releasing the $NO_x$ absorbed in the $NO_x$ absorbent when the exhaust gas composition is $1 \geq$ lambda; and
a platinum group metal catalyst coated onto a substrate upstream of the ceramic wall flow particulate filter for oxidising NO to $NO_2$ at least when the composition of the exhaust gas is lambda>1, wherein the uncoated ceramic wall flow particulate filter has a porosity of >40% and a mean pore size of 8-25 μm and the washcoat composition has a D50 less than or equal to 8 μm.

2. An exhaust system according to claim 1, wherein the porosity of the uncoated filter is from 42-60%.

3. An exhaust system according to claim 1, wherein the mean pore size of the uncoated filter is from 11-22 μm.

4. An exhaust system according to claim 1, wherein the platinum group metal in the platinum group metal catalyst is platinum and palladium.

5. An exhaust system according to claim 1, wherein the washcoat composition further comprises an alumina support.

6. An exhaust system according to claim 1, wherein the washcoat composition further comprises a support of a mixed metal oxide or a composite metal oxide comprising two or more metals selected from the group consisting of aluminium, silicon, chromium, zirconium, titanium and cerium.

7. An exhaust system according to claim 1, wherein the ceramic wall flow particulate filter further comprises rhodium.

8. An exhaust system according to claim 4, wherein the ceramic wall flow particulate filter has exit channels and the rhodium is coated on the exit channels.

9. An internal combustion engine including an exhaust system according to claim 1.

10. An engine according to claim 9, wherein the engine is a diesel engine.

11. An engine according to claim 10, wherein the diesel engine is a heavy duty diesel engine.

12. A vehicle including an internal combustion engine according to claim 9.

13. A method of treating an exhaust gas of an internal combustion engine, which method comprising the steps of:

oxidising NO in the exhaust gas to $NO_2$ at least when the composition of the exhaust gas is lambda>1;
downstream of the oxidizing step, trapping particulate on a ceramic wall flow filter having a porosity of >40% and a mean pore size of 8-25 μm and coated throughout with a catalytic washcoat composition having a D50 less than or equal to 8 μm, the washcoat composition comprising: (i) a $NO_x$ absorbent and (ii) an oxidation catalyst comprising a platinum group metal selected from the group consisting of platinum, palladium, and a mixture thereof;
when the composition of the exhaust gas is lambda>1, oxidising NO to $NO_2$ on the filter and absorbing the $NO_2$ in the NO absorbent, or
when the exhaust gas composition is $1 \geq$ lambda, releasing the absorbed $NO_x$ as $NO_2$; and
combusting particulate trapped on the filter in the presence of $NO_2$.

14. A method according to claim 13, wherein the porosity of the filter is from 42-60%.

15. A method according to claim 13, wherein the mean pore size of the filter is from 11-22 μm.

16. A method according to claim 13, wherein the step of combusting particulate is done at exhaust gas temperatures of up to 400° C.

17. A method according to claim 13, wherein the platinum group metal in the platinum group metal catalyst is platinum and palladium.

18. A method according to claim 13, wherein the $NO_x$ absorbent comprises a metal selected from the group consisting of an alkali metal, an alkaline earth metal, a rare earth metal, and a mixture thereof.

19. method according to claim 13, wherein the washcoat composition further comprises rhodium.

20. A method according to claim 19, wherein the wall flow filter has exit channels and the exhaust gas contacts the rhodium in the exit channels of the filter.

* * * * *

UNITED STATES PATENT AND TRADEMARK OFFICE
CERTIFICATE OF CORRECTION

| | | |
|---|---|---|
| PATENT NO. | : 7,832,203 B2 | Page 1 of 1 |
| APPLICATION NO. | : 11/281089 | |
| DATED | : November 16, 2010 | |
| INVENTOR(S) | : Chiffey et al. | |

It is certified that error appears in the above-identified patent and that said Letters Patent is hereby corrected as shown below:

At column 1, lines 11 and 12:

"British Patent Application No. 0126346.6, filed November 2, 2001."

should read:

--British Patent Application No. 0125890.4, filed October 27, 2001.--

Signed and Sealed this
Fourth Day of October, 2011

David J. Kappos
*Director of the United States Patent and Trademark Office*